United States Patent
Goebbel et al.

(10) Patent No.: US 7,378,536 B2
(45) Date of Patent: May 27, 2008

(54) METHOD FOR PRODUCING PROPYLENE OXIDE

(75) Inventors: Hans-Georg Goebbel, Kallstadt (DE); Peter Bassler, Viernheim (DE); Joaquim Henrique Teles, Otterstadt (DE); Peter Rudolf, Ladenburg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 236 days.

(21) Appl. No.: 10/553,441

(22) PCT Filed: Apr. 16, 2004

(86) PCT No.: PCT/EP2004/004104

§ 371 (c)(1),
(2), (4) Date: Oct. 14, 2005

(87) PCT Pub. No.: WO2004/092150

PCT Pub. Date: Oct. 28, 2004

(65) Prior Publication Data

US 2006/0205964 A1  Sep. 14, 2006

(30) Foreign Application Priority Data

Apr. 16, 2003 (DE) .............................. 103 17 519

(51) Int. Cl.
*C07D 301/03* (2006.01)

(52) U.S. Cl. .......................... 549/531; 203/22; 203/23; 203/24; 203/25

(58) Field of Classification Search ................ 549/531, 549/538; 203/23, 22, 24, 25
See application file for complete search history.

(56) References Cited

U.S. PATENT DOCUMENTS 2,509,136 A * 5/1950 Cornell ........................ 203/3
6,024,840 A * 2/2000 Rueter ........................ 203/50

FOREIGN PATENT DOCUMENTS

| EP | 0 311 983 | 4/1989 |
| EP | 0 405 978 | 5/1993 |
| WO | 98/55228 | 12/1998 |
| WO | 98/55430 | 12/1998 |
| WO | 98/55229 | 11/1999 |
| WO | 00/07965 | 2/2000 |
| WO | 02/14298 | 2/2002 |

OTHER PUBLICATIONS

Meier, W.M. et al., Atlas of Zeolite Structure Types, Elsevier 4th Ed., London, 1996.

* cited by examiner

*Primary Examiner*—Bernard Dentz
*Assistant Examiner*—David E Gallis
(74) *Attorney, Agent, or Firm*—Oblon, Spivak, McClelland, Maier & Neustadt, P.C.

(57) ABSTRACT

Process for preparing propylene oxide, which comprises at least the steps (iii) and (iv)
(iii) separating off propylene oxide from a mixture (M1) comprising propylene oxide and at least one solvent by distillation in a distillation column, giving a bottom stream and a vapor stream consisting essentially of propylene oxide;
(iv) compressing the vapor stream obtained in (iii) by means of at least one compressor to give a compressed vapor.

18 Claims, No Drawings

METHOD FOR PRODUCING PROPYLENE OXIDE

The present invention relates to a process for preparing propylene oxide, in which a mixture consisting essentially of propylene oxide and at least one solvent, preferably methanol, is worked up by distillation. In this work-up, a vapor from the distillation column, which consists essentially of propylene oxide, is compressed to give a gaseous vapor which is under a particular pressure. In a preferred embodiment, the energy contained in the compressed vapor is at least partly returned to the distillation process, for example for operating at least one vaporizer of the distillation column. In further preferred embodiments, the present invention encompasses further aspects which have a positive effect on the energy balance of the overall process.

In the numerous publications on the subject of the preparation of propylene oxide, there are only a few which are concerned with integrated processes in which the energy of the vapor obtained in a distillation step is usefully returned to the process. This applies particularly to processes in which propylene oxide is separated off from solvents or traces of solvent by distillation.

WO 02/14298 A1 describes a process for the continuous preparation of an olefin oxide. In the context of this process step, it is disclosed that the heat of condensation obtained at the top of a column can be recovered for one or all distillation processes of the overall process. In the column in question, a mixture comprising solvent, oxygen and inert gas is separated by distillation. Specific procedures for recirculating the heat of condensation are not disclosed.

WO 00/07965 describes a process for preparing propylene oxide, in which a mixture of propene, propylene oxide and methanol is separated off from a mixture via the top of a distillation column, with the reflux necessary for the separation in the column being condensed in a partial condenser at the top of the column.

If methanol, for example, is used as solvent in the preparation of propylene oxide from propene, it is generally advantageous for this to be used in the reaction section, i.e. for the reaction of propene with a hydroperoxide such as hydrogen peroxide, particularly when a titanium silicalite catalyst of the TS-1 type is used as catalyst for the reaction. On the other hand, the presence of methanol makes purification of the propylene oxide more difficult.

At atmospheric pressure or superatmospheric pressures, essentially in the range from 1 to 5 bar, propylene oxide and methanol can be separated by distillation only when a distillation column having a very large number of theoretical plates is used and a very high reflux ratio is set at the same time, owing to the entraining azeotrope.

The separation task is simpler at lower pressures, but the low pressure has an adverse effect on the condensation temperature since the condensation temperature, which can, for example, be in the region of 15° C. depending on the pressure, requires provision of a high refrigeration power for condensation. Especially on an industrial scale, this incurs tremendous costs.

It is an object of the present invention to provide a process which, compared to the processes described in the prior art for preparing propylene oxide, has a significantly improved energy balance.

The present invention accordingly provides a process for preparing propylene oxide, which comprises at least the steps (iii) and (iv)

(iii) separating off propylene oxide from a mixture (M1) comprising propylene oxide and at least one solvent by distillation in a distillation column, giving a bottom stream and a vapor stream consisting essentially of propylene oxide;

(iv) compressing the vapor stream obtained in (iii) by means of at least one compressor to give a compressed vapor.

The solvent or solvents present in the mixture (M1) in (iii) can in principle be any solvent(s) which is/are used in the process for preparing propylene oxide.

Particularly preferred solvents are, for example:

water;

alcohols, preferably alcohols having less than 6 carbon atoms, more preferably methanol, ethanol, propanols, butanols, pentanols;

diols or polyols, preferably those having less than 6 carbon atoms;

ethers such as diethyl ether, tetrahydrofuran, dioxane, 1,2-diethoxyethane, 2-methoxyethanol;

esters such as methyl acetate or butyrolactone;

amides such as dimethylformamide, dimethylacetamide, N-methylpyrrolidone;

ketones such as acetone;

nitrites such as acetonitrile;

or mixtures of two or more of the compounds mentioned.

Very particular preference is given to using a mixture (M1) comprising propylene oxide together with methanol or water or methanol and water as solvent in the process of the present invention. The mixture (M1) more preferably comprises methanol as solvent.

Accordingly, the present invention provides a process as described above in which the at least one solvent is methanol.

The solvent content and particularly preferably the methanol content of the propylene oxide separated off from the mixture (M1) in (iii) is generally not more than 500 ppm, preferably not more than 200 ppm, more preferably not more than 100 ppm, more preferably not more than 50 ppm, more preferably not more than 20 ppm, particularly preferably not more than 15 ppm and very particularly preferably not more than 10 ppm, in each case based on the total weight of the propylene oxide fraction separated off.

As distillation column, it is essentially possible to use any column. Particular preference is given to a distillation column configured as a packed column, more preferably a packed column containing ordered packing. Such a packed column has a high separation efficiency per meter of packing and displays only a very small pressure drop.

While the ordered packing mentioned can essentially be of any type, preference is given to packing which has a specific surface area in the range of from 100 to 750 $m^2/m^3$. It is possible to use sheet metal packing, for example from Montz (type B1 100 to B1 500) or from Sulzer ChemTech (Mellapak 125 to Mellapak 750), or mesh packing from Montz (type A3 500 to A3 750) or from Sulzer ChemTech (type BX or CY). The unit $m^2/m^3$ refers to the geometric surface area of the material forming the packing per cubic meter of packing.

While the distillation in (iii) can generally be carried out under all suitable conditions, according to the present invention preference is given to embodiments of the distillation in (iii) in which the mixture (M1) is fractionated under reduced pressure. For the purposes of the present invention, the term "distillation under reduced pressure" refers to any distillation which is carried out at a pressure of less than 1.013 bar.

The distillation in (iii) is therefore generally carried out at pressures of less than 1.013 bar, preferably in a range up to 1 bar, more preferably in a range of from 300 to 900 mbar, more preferably in a range of from 400 to 800 mbar and particularly preferably in a range of from 450 to 750 mbar.

Accordingly, the present invention also provides a process as described above in which the distillation column used for the fractional distillation in (iii) is operated at a pressure in the range of from 450 to 750 mbar.

In step (iv) of the process of the present invention, the vapor obtained at the top of the distillation column, which consists essentially of propylene oxide, is compressed. This compression can generally be carried out using any suitable methods. In particular, the vapor can be compressed mechanically or thermally, with compression being able to be carried out in one or more apparatuses. It is thus possible to compress the vapor mechanically in at least one compression apparatus or to compress the vapor thermally in at least one compression apparatus or firstly to compress the vapor mechanically in at least one compression apparatus and then to compress the vapor thermally in at least one compression apparatus or firstly to compress the vapor thermally in at least one compression apparatus and then to compress the vapor mechanically in at least one compression apparatus.

Apparatuses suitable for mechanical compression are, for instance, rotary piston compressors, screw compressors, turbocompressors having an axial or radial construction, diaphragm-type compressors or blowers. For the purposes of the present invention, compression can be carried out using one of these apparatuses or a combination of two or more of these apparatuses, with each of the compressors used being able to have one or more stages.

An example of an apparatus for thermal compression is a steam ejector which can be equipped with a fixed or regulatable driving nozzle.

For the purposes of the present invention, the vapor is particularly preferably compressed mechanically, once again preferably in a single apparatus. Preference is in turn given to a turbocompressor, very particularly preferably a single-stage single-screw compressor.

Accordingly, the present invention also provides a process as described above in which compression of the vapor is carried out using a turbocompressor.

In a more preferred embodiment of the process of the present invention, the vapor is compressed by means of the preferred mechanical compressor so that the vapor has a pressure in the range of generally from 1.5 to 5 bar, preferably from 2 to 4 bar and particularly preferably from 2.5 to 3.5 bar, after leaving the compressor.

In general, the vapor is brought by compression to a temperature which is at least 1° C. higher than the temperature of the medium vaporizing in the bottom of the distillation column. The vapor is preferably brought by compression to a temperature which is from 2 to 25° C., more preferably from 5 to 20° C. and particularly preferably from 8 to 20° C., higher than the temperature of the medium vaporizing in the distillation column.

Accordingly, the present invention also provides a process as described above in which the vapor is compressed to a pressure in the range of from 2 to 5 bar in (iv) and the compressed vapor has a temperature which is in a range of from 8 to 20° C. above the temperature of the medium vaporizing in the distillation column in (iii).

As a result of the compression step according to the present invention, the process of the present invention makes possible the above-described favorable pressure range below 1.013 bar, preferably the range from 450 to 750 mbar, for the distillation without having to accept the disadvantage of a low condensation temperature and the high refrigeration power which then has to be made available.

Depending on the composition of the feed and the required purity of the propylene oxide in respect of the residual concentration of solvent, preferably methanol, the compressor power is in the range of from 3 to 9 MW. The corresponding condensation/refrigeration power which would have to be employed at a temperature in the range of from 12 to 20° C. would be in a range of from 15 to 25 MW.

The energy additionally stored in the vapor as a result of compression can, for example, preferably be fed to any process, with recirculation into the process of the present invention being preferred. In general, all or part of the quantity of energy can be introduced into any process step. Particular preference is given to recirculation of at least part of the energy stored in the compressed vapor to the distillation step (iii). Particular preference is in this case given to at least one vaporizer of the distillation column, for example at least one intermediate vaporizer or the main vaporizer or at least one intermediate vaporizer and the main vaporizer, being operated by means of the energy stored in the compressed vapor. In this way, a heat pump is realized in the process of the present invention as a result of this integrated operation of the process.

In a very particularly preferred embodiment, the compressed gaseous vapor is liquefied in at least one condenser and the heat of condensation is at least partly used for operating at least one of the abovementioned vaporizers. Particular preference is given to the operation of the main vaporizer of the distillation column used in (iii).

Accordingly, the present invention also provides a process as described above which additionally comprises the step (v)

(v) condensing the vapor obtained in (iv) and returning at least part of the heat of condensation to at least one vaporizer used in the distillation column employed in (iii).

The condensation in (v) is carried out in a vaporizer which can have essentially any configuration. Examples of embodiments of vaporizers are natural convection vaporizers, forced circulation vaporizers or falling film vaporizers. For the purposes of the present invention, preference is given to using a vaporizer which is configured as a natural convection vaporizer.

The cooled condensate leaving the condenser or condensers of (v) has, in the process of the present invention, a temperature of generally from 40 to 75° C., preferably from 45 to 70° C. and particularly preferably from 45 to 65° C.

It is generally possible to operate the vaporizer using only the energy recovered as described above from the condensation of the compressed vapor. In a more preferred embodiment of the process of the present invention, at least one further vaporizer which serves to compensate differences in the condensation and vaporization enthalpy and accordingly functions as a supplementary or secondary vaporizer is additionally provided.

This/these additional vaporizer or vaporizers can have essentially any configuration. Examples of embodiments of the additional vaporizer or vaporizers are natural convection vaporizers, forced circulation vaporizers or falling film vaporizers. For the purposes of the present invention, preference is given to using a vaporizer which is configured as a natural convection vaporizer.

In a more preferred embodiment of the process of the present invention, at least part of the condensate obtained in (v) is cooled further in at least one further heat exchanger so as to obtain energy which can be passed to any other process or preferably be recirculated within the process of the present invention.

This part of the condensate is preferably cooled in the further heat exchanger or exchangers to a temperature in the range from 10 to 30° C., particularly preferably in the range from 12 to 20° C.

In a very particularly preferred embodiment, the cooled condensate leaving this heat exchanger or exchangers is returned as reflux to the distillation column used in (iii).

Accordingly, the present invention also provides a process as described above which additionally comprises the step (vi)

(vi) cooling at least part of the condensate obtained in (v) to a temperature in the range from 10 to 30° C. in at least one heat exchanger and returning this part of the cooled condensate as reflux to the distillation column used in (iii).

In the process of the present invention, the refrigeration power employed in the heat exchanger of (vi) for cooling the condensate is preferably provided by at least a part of the process of the present invention. For example, it is conceivable for the refrigeration power required in the heat exchanger of (vi) to be taken from a refrigerant which at another point of the process once again takes up the quantity of cold withdrawn in this way. However, it is also conceivable for the refrigeration power taken up in the heat exchanger to be transferred directly from a material or mixture which can generally be in any possible state of matter. For example, preference is given, in the process of the present invention, to depressurizing a compressed stream into a compartment of the heat exchanger and at least partly, preferably completely, vaporizing it and transferring the resulting refrigeration power to the condensate present in another compartment of the heat exchanger. Preference is in turn given to an embodiment in which this compressed stream is a compressed propene stream. In particular, this propene stream is a compressed propene stream which is firstly, as described above, depressurized into the heat exchanger and vaporized in the heat exchanger and is subsequently used in step (i), which is described below, of the process of the present invention.

The compressed propene stream is particularly preferably vaporized completely in the vaporizer or vaporizers used in (vi).

Accordingly, the present invention also provides a process as described above in which the propene compressed in the vaporizer or vaporizers used in (vi) is vaporized completely with depressurization.

For example, the propene stream has preferably been compressed to a pressure in the range from 20 to 35 bar at a temperature in the range from 5 to 30° C., preferably from 10 to 30° C., more preferably from 15 to 30° C. and particularly preferably from 20 to 30° C., and is, according to the present invention depressurized in step (vi) to a pressure in the range from 4 to 10 bar, preferably from 5 to 9 bar and more preferably from 5 to 8 bar, and vaporized completely by introduction of heat. For example, about half the cold of expansion of the propene is produced by means of this step.

The depressurization of the compressed stream in (vi) is into a heat exchanger which can have essentially any configuration. Examples of configurations of the heat exchanger are shell-and-tube heat exchangers, coil heat exchangers or plate heat exchangers. For the purposes of the present invention, preference is given to using a heat exchanger which is configured as a shell-and-tube heat exchanger.

The bottom stream obtained from (iii) can, according to a more preferred embodiment of the process of the present invention, likewise be used for improving the energy integration of the process of the present invention even further.

For this purpose, the quantity of heat contained in the bottom stream obtained from (iii) is at least partly used for heating the mixture (M1) before it is introduced into the distillation column in (iii). Particular preference is here given to using a heat exchanger configured as a countercurrent heat exchanger (plate heat exchanger).

Accordingly, the present invention also provides a process as described above in which the energy stored in the bottom stream obtained from (iii) is at least partly used for heating the mixture (M1) before it is fractionally distilled in (iii).

The mixture (M1) used in (iii) results from essentially any process steps in the preparation of propylene oxide, provided that a mixture (M1) as described above is obtained.

The mixture (M1) is particularly preferably obtained from a process in which propene is reacted with a hydroperoxide in methanol as solvent in the presence of a zeolite catalyst.

In the process of the present invention, the propene is reacted with at least one hydroperoxide. For the purposes of the present patent application, the term "hydroperoxide" refers to a compound of the formula ROOH. Details regarding the preparation of hydroperoxides and regarding hydroperoxides which can be used, inter alia, in the process of the present invention may be found in DE-A 198 35 907, whose relevant contents are incorporated by reference into the disclosure of the present patent application. Examples of hydroperoxides which can be used according to the present invention include tert-butyl hydroperoxide, ethylbenzene hydroperoxide, tert-amyl hydroperoxide, cumene hydroperoxide, cyclohexyl hydroperoxide, methylcyclohexyl hydroperoxide, tetrahydronaphthalene hydroperoxide, isobutylbenzene hydroperoxide, ethylnaphthalene hydroperoxide, peracids such as peracetic acid or hydrogen peroxide. Mixtures of two or more hydroperoxides can also be used according to the present invention. For the purposes of the present invention, preference is given to using hydrogen peroxide, more preferably an aqueous hydrogen peroxide solution, as hydroperoxide.

The zeolite catalysts which can be used for the purposes of the present invention are subject to no particular restrictions.

It is known that zeolites are crystalline aluminosilicates having ordered channel and cage structures and containing micropores which are preferably smaller than about 0.9 nm. The network of such zeolites is made up of $SiO_4$ and $AlO_4$ tetrahedra which are joined via shared oxygen bridges. An overview of known structures may be found, for example, in W. M. Meier, D. H. Olson and Ch. Baerlocher, "Atlas of Zeolite Structure Types", Elsevier, 5th edition, Amsterdam 2001.

Zeolites which contain no aluminum and in which part of the Si(IV) in the silicate lattice is replaced by titanium as Ti(IV) are also known. These titanium zeolites, in particular those having a crystal structure of the MFI type, and possible ways of preparing them are described, for example, in EP-A 0 311 983 or EP-A 0 405 978. Apart from silicon and titanium, such materials can further comprise additional elements such as aluminum, zirconium, tin, iron, cobalt, nickel, gallium, germanium, boron or small amounts of fluorine. In the zeolite catalysts the titanium of the zeolite can be partly or completely replaced by vanadium, zirconium, chromium or niobium or a mixture of two or more thereof. The molar ratio of titanium and/or vanadium, zirconium, chromium or niobium to the sum of silicon and titanium and/or vanadium and/or zirconium and/or chromium and/or niobium is generally in the range from 0.01:1 to 0.1:1.

Titanium zeolites, in particular those having a crystal structure of the MFI type, and possible ways of preparing them are described, for example, in WO 98/55228, EP-A 0 311 983 or EP-A 0 405 978, whose relevant contents are fully incorporated into the disclosure of the present patent application.

It is known that titanium zeolites having an MFI structure can be identified via a particular X-ray diffraction pattern and additionally via a lattice vibration band in the infrared region (IR) at about 960 cm$^{-1}$ and in this way differ from alkali metal titanates or crystalline and amorphous $TiO_2$ phases.

Specific mention may be made of titanium-, germanium-, tellurium-, vanadium-, chromium-, niobium-, and zirconium-containing zeolites having a pentasil zeolite structure, in particular the types which can be assigned X-ray-crystallographically to the ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WIE, WEN, YUG, ZON structure or to mixed structures comprising two or more of the abovementioned structures. Furthermore, titanium-containing zeolites having the ITQ-4, SSZ-24, TTM-1, UTD-1, CIT-1 or CIT-5 structure are also conceivable for use in the process of the present invention. Further titanium-containing zeolites which may be mentioned are those of the ZSM-4 or ZSM-12 structure.

For the purposes of the present invention, particular preference is given to using Ti zeolites having an MFI or MEL structure or an MFI/MEL mixed structure. Further preference is given to the specific Ti-containing zeolite catalysts which are generally referred to as "TS-1", "TS-2", "TS-3" and also Ti zeolites having a framework structure isomorphous with beta-zeolite. For the purposes of the present invention, very particular preference is given to a zeolite catalyst of the TS-1 type.

After the reaction of the propene with, preferably, hydrogen peroxide to give a mixture (M0) comprising propylene oxide, unreacted propene and methanol, unreacted propene is preferably separated off from this mixture (M0), preferably by distillation.

Accordingly, the present invention also provides a process as described above which additionally comprises the steps (i) and (ii)
(i) reacting propene with hydrogen peroxide in the presence of a titanium silicalite catalyst and methanol as solvent to give a mixture (M0) comprising propylene oxide, unreacted propene and methanol;
(ii) separating off the unreacted propene from the mixture (M0) to give a mixture (M1) comprising propylene oxide and methanol.

The reaction of propene with hydrogen peroxide in the presence of methanol and the titanium silicalite catalyst can be carried out in one, two or more stages, particularly preferably in two stages.

A two-stage reaction takes place, for example, as follows:
(a) the hydrogen peroxide is reacted with propene to give a mixture comprising propylene oxide and unreacted hydrogen peroxide;
(b) the unreacted hydrogen peroxide is separated off from the mixture resulting from stage (a);
(c) the hydrogen peroxide which has been separated off in stage (b) is reacted with propene.

Accordingly, the reaction of propene with hydrogen peroxide takes place, as indicated, in two stages (a) and (c), with a separation stage (b) in between.

For the purposes of the present invention, the hydrogen peroxide can be separated off in the separation stage (b) using all customary separation methods known from the prior art.

The hydrogen peroxide is preferably separated off by distillation. Depending on the requirements of the process, it can be separated off in one or more distillation columns. Preference is given to using one distillation column in a separation stage.

In the process of the present invention, the reaction of propene with hydrogen peroxide takes place in a reactor which is suitable for this purpose. Starting materials used for the reaction are propene, hydrogen peroxide and methanol. In this process, the starting materials can be fed individually into the reactor or are preferably combined to form one stream and fed in this form into the reactor. In the process of the present invention, preference is given to feeding a stream consisting of the combination of the starting materials into the reactor. Preference is in this case given to a stream in which the concentrations of the individual starting materials in the stream are selected so that the stream is liquid and consists of a single phase.

In a further, preferred embodiment, it is possible to carry out the reaction in stages (a) and (c) in two separate reactors.

As reactors, it is of course possible to use all conceivable reactors which are best suited to the respective reaction. In this context, the term "a reactor" is not restricted to a single vessel. Rather, it is also possible to use a cascade of stirred vessels as reactor.

Preference is given to using fixed-bed reactors as reactors. Greater preference is given to using fixed-bed tube reactors as fixed-bed reactors, with at least one of the reactors also being able to be operated in the suspension mode.

In the case of the reactions in stages (a) and (c) being carried out in two separate reactors, particular preference is given to using one isothermal fixed-bed tube reactor and one adiabatic fixed-bed reactor. Preference is given to using the isothermal fixed-bed tube reactor in stage (a) and the adiabatic fixed-bed reactor in stage (b).

In a preferred embodiment of the process of the present invention, the mixture (M1) comprises from 5 to 15% by weight, preferably from 6 to 12% by weight and particularly preferably from 8 to 10.5% by weight, of propylene oxide and from 55 to 85% by weight, preferably from 60 to 80% by weight and particularly preferably from 65 to 75% by weight, of methanol.

The term "a vapor stream consisting essentially of propylene oxide" as used in the context of the present invention with regard to the vapor stream resulting from (iii) relates to a vapor stream having a solvent content of not more than 500 ppm, preferably not more than 200 ppm, more preferably not more than 100 ppm, more preferably not more than 50 ppm, more preferably not more than 20 ppm, particularly preferably not more than 15 ppm and very particularly preferably not more than 10 ppm, in each case based on the total weight of the vapor stream resulting from (iii).

Compared to the processes of the prior art, an advantage of the process of the present invention is, inter alia, that it can be carried out at lower reflux ratios. According to the present invention, these reflux ratios are preferably in the range of from 4 to 10. Preferred reflux ratios are, among others, 4, 5, 6, 7, 8, 9 or 10.

The present invention is illustrated by the following examples.

EXAMPLES

Comparative Example 1

Conventional Fractionation to Give a Propylene Oxide Fraction Having a Methanol Content of 20 ppm Using the process disclosed in WO 00/07965, propylene oxide is prepared from propene by reaction with hydrogen peroxide in methanol as solvent using a titanium zeolite catalyst of the TS-1 type. Propylene oxide is separated off by distillation from the mixture having the composition described below obtained after removal of the excess propene in such a way that the resulting propylene oxide fraction has a methanol concentration of 20 ppm.

Composition of the mixture to be separated:
Low boilers: 0.2% by weight
Propylene oxide: 9.3% by weight
Methanol: 70% by weight
Methoxypropanols: 0.5% by weight
Water: 18% by weight
High boilers: 2% by weight The distillation is carried out at a pressure of 1.5 bar, so that the vapor can be condensed in the condenser by means of available river water at a temperature of about 42° C. The methanol concentration of the propylene oxide stream is 20 ppm. The optimized separation proceeds at a reflux ratio of 18 and has an energy consumption for the above separation of 2 650 kWh/t (propylene oxide fraction).

Comparative Example 2

Conventional Fractionation to Give a Propylene Oxide Fraction Having a Methanol Content of 10 ppm Using the process disclosed in WO 00/07965, propylene oxide is prepared from propene by reaction with hydrogen peroxide in methanol as solvent using a titanium zeolite catalyst of the TS-1 type. Propylene oxide is separated off by distillation from the mixture having the composition described below obtained after removal of the excess propene in such a way that the resulting propylene oxide fraction has a methanol concentration of 10 ppm.

Composition of the mixture to be separated:
Low boilers: 0.2% by weight
Propylene oxide: 9.3% by weight
Methanol: 70% by weight
Methoxypropanols: 0.5% by weight
Water: 18% by weight
High boilers: 2% by weight The distillation is carried out at a pressure of 1.5 bar, so that the vapor can be condensed in the condenser by means of available river water at a temperature of about 42° C. The methanol concentration of the propylene oxide stream is 10 ppm. The optimized separation proceeds at a reflux ratio of 23 and has an energy consumption for the above separation of 3 280 kWh/t (propylene oxide fraction).

Example 1

Fractionation According to the Present Invention to Give a Propylene Oxide Fraction Having a Methanol Content of 20 ppm Using the process disclosed in WO 00/07965, propylene oxide is prepared from propene by reaction with hydrogen peroxide in methanol as solvent using a titanium zeolite catalyst of the TS-1 type. Propylene oxide is separated off by distillation from the mixture having the composition described below obtained after removal of the excess propene in such a way that the resulting propylene oxide fraction has a methanol concentration of 20 ppm.

Composition of the mixture to be separated:
Low boilers: 0.2% by weight
Propylene oxide: 9.3% by weight
Methanol: 70% by weight
Methoxypropanols: 0.5% by weight
Water: 18% by weight
High boilers: 2% by weight The distillation is carried out at a pressure of 500 mbar using a vapor compressor and using the compressed vapor for operating the natural convection vaporizer of the column. The vapor is compressed to a pressure of about 2.8 bar by means of a turbocompressor (single-stage turbine compressor having 2×4 rotors), resulting in the compressed vapor having a temperature of about 68° C. The electric energy consumption of the compressor is about 6 MW. The vaporization temperature in the convection vaporizer of the column is about 54° C.

The reflux ratio in this separation (residual methanol concentration of 20 ppm in the propylene oxide stream) is about 8. The additional energy requirement for the separation in addition to that introduced by thermal coupling is about 180 kWh/t (propylene oxide fraction).

Example 2

Fractionation According to the Present Invention to Give a Propylene Oxide Fraction Having a Methanol Content of 10 ppm Using the process disclosed in WO 00/07965, propylene oxide is prepared from propene by reaction with hydrogen peroxide in methanol as solvent using a titanium zeolite catalyst of the TS-1 type. Propylene oxide is separated off by distillation from the mixture having the composition described below obtained after removal of the excess propene in such a way that the resulting propylene oxide fraction has a methanol concentration of 10 ppm.

Composition of the mixture to be separated:
Low boilers: 0.2% by weight
Propylene oxide: 9.3% by weight
Methanol: 70% by weight
Methoxypropanols: 0.5% by weight
Water: 18% by weight
High boilers: 2% by weight The distillation is carried out at a pressure of 500 mbar using a vapor compressor and using the compressed vapor for operating the natural convection vaporizer of the column. The vapor is compressed to a pressure of about 2.8 bar by means of a turbocompressor (single-stage turbine compressor having 2×4 rotors), resulting in the compressed vapor having a temperature of about 68° C. The electric energy consumption of the compressor is about 8 MW. The vaporization temperature in the convection vaporizer of the column is about 54° C.

The reflux ratio in this separation (residual methanol concentration of 10 ppm in the propylene oxide stream) is about 9. The additional energy requirement for the separation in addition to that introduced by thermal coupling is about 200 kWh/t (propylene oxide fraction).

We claim:

1. A process for preparing propylene oxide, which comprises at least the steps (iii) and (iv)
    (iii) separating off propylene oxide from a mixture (M1) comprising propylene oxide and at least one solvent by distillation in a distillation column, giving a bottom stream and a vapor stream consisting essentially of propylene oxide, wherein the distillation is carried out at a pressure of less than 1.013 bar;
    (iv) compressing the vapor stream obtained in (iii) by means of at least one compressor to give a compressed vapor,
    wherein the solvent content of the vapor stream in (iii) is not more than 500 ppm.

2. A process as claimed in claim 1, wherein the at least one solvent is methanol.

3. A process as claimed in claim 1, wherein the distillation column used for the separation by distillation in (iii) is operated at a pressure in the range of from 450 to 750 mbar.

4. A process as claimed in claim 1, wherein the compression of the vapor is carried out using a turbocompressor.

5. A process as claimed in claim 1, wherein the vapor is compressed to a pressure in the range of from 2 to 5 bar in (iv) and the compressed vapor has a temperature which is in a range of from 8 to 20° C. above the temperature of the medium vaporizing in the distillation column in (iii).

6. A process as claimed in claim 1, which additionally comprises the step (v)
    (v) condensing the vapor obtained in (iv) and returning at least part of the heat of condensation to at least one vaporizer used in the distillation column employed in (iii).

7. A process as claimed in claim 6, which additionally comprises the step (vi)
    (vi) cooling at least part of the condensate obtained in (v) to a temperature in the range of from 10 to 30° C. in at least one heat exchanger and returning this part of the cooled condensate as reflux to the distillation column used in (iii).

8. A process as claimed in claim 7, wherein further comprising:
    depressurizing a compressed propene stream into a compartment of the heat exchanger used in (vi), and
    vaporizing the depressurized compressed propene completely;
    wherein a resulting refrigeration power is transferred to the condensate present in another compartment of the heat exchanger.

9. A process as claimed in claim 1, wherein the energy stored in the bottom stream obtained in (iii) is at least partly used for heating the mixture (M1) before it is fractionally distilled in (iii).

10. A process as claimed in claim 1, which additionally comprises the steps (i) and (ii)
    (i) reacting propene with hydrogen peroxide in the presence of a titanium silicalite catalyst and methanol as solvent to give a mixture (M0) comprising propylene oxide, unreacted propene and methanol;
    (ii) separating off the unreacted propene from the mixture (M0) to give a mixture (M1) comprising propylene oxide and methanol.

11. A process for preparing propylene oxide, which comprises at least the steps (iii) and (iv)
    (iii) separating off propylene oxide from a mixture (M1) comprising propylene oxide and at least one solvent by distillation in a distillation column, giving a bottom stream and a vapor stream consisting essentially of propylene oxide, wherein the distillation is carried out at a pressure of less than 1.013 bar;
    (iv) compressing the vapor stream obtained in (iii) by means of at least one compressor to give a compressed vapor,
    wherein the at least one solvent is methanol, and wherein the solvent content of the vapor stream in (iii) is not more than 500 ppm.

12. A process as claimed in claim 11, wherein the distillation column used for the separation by distillation in (iii) is operated at a pressure in the range of from 450 to 750 mbar.

13. A process as claimed in claim 11, wherein the compression of the vapor is carried out using a turbocompressor.

14. A process as claimed in claim 11, wherein the vapor is compressed to a pressure in the range of from 2 to 5 bar in (iv) and the compressed vapor has a temperature which is in a range of from 8 to 20° C. above the temperature of the medium vaporizing in the distillation column in (iii).

15. A process as claimed in claim 11, which additionally comprises the step (v)
    (v) condensing the vapor obtained in (iv) and returning at least part of the heat of condensation to at least one vaporizer used in the distillation column employed in (iii).

16. A process as claimed in claim 15, which additionally comprises the step (vi):
    (vi) cooling at least part of the condensate obtained in (v) to a temperature in the range of from 10 to 30° C. in at least one heat exchanger and returning this part of the cooled condensate as reflux to the distillation column used in (iii).

17. A process as claimed in claim 16, further comprising:
    depressurizing a compressed propene stream into a compartment of the heat exchanger used in (vi), and
    vaporizing the depressurized compressed propene completely;
    wherein a resulting refrigeration power is transferred to the condensate present in another compartment of the heat exchanger.

18. A process for preparing propylene oxide, which comprises at least the steps (iii) and (iv)
    (iii) separating off propylene oxide from a mixture (M1) comprising propylene oxide and at least one solvent by distillation in a distillation column, giving a bottom stream and a vapor stream consisting essentially of propylene oxide, wherein the distillation is carried out at a pressure of less than 1.013 bar, and wherein the at least one solvent is methanol, and the methanol content of the vapor stream is not more than 500 ppm;
    (iv) compressing the vapor stream obtained in (iii) by means of at least one compressor to give a compressed vapor,
    which additionally comprises the steps (i) and (ii)
    (i) reacting propene with hydrogen peroxide in the presence of a titanium silicalite catalyst and methanol as solvent to give a mixture (M0) comprising propylene oxide, unreacted propene and methanol;

(ii) separating off the unreacted propene from the mixture (M0) to give a mixture (M1) comprising propylene oxide and methanol,
and the steps (v) and (vi)
(v) condensing the vapor obtained in (iv) and returning at least part of the heat of condensation to at least one vaporizer used in the distillation column employed in (iii), and (vi) cooling at least part of the condensate obtained in (v) to a temperature in the range of from 10 to 30° C. in at least one heat exchanger and returning this part of the cooled condensate as reflux to the distillation column used in (iii).

* * * * *